(12) United States Patent
Srinivas et al.

(10) Patent No.: US 11,517,308 B2
(45) Date of Patent: *Dec. 6, 2022

(54) LOADING UNIT FOR A SURGICAL STAPLING INSTRUMENT

(71) Applicant: Covidien LP, Mansfield, MA (US)

(72) Inventors: Jitendra Bhargava Srinivas, Hyderabad (IN); Roanit Fernandes, Hyderabad (IN)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/039,375

(22) Filed: Sep. 30, 2020

(65) Prior Publication Data

US 2021/0007738 A1 Jan. 14, 2021

Related U.S. Application Data

(63) Continuation of application No. 16/047,706, filed on Jul. 27, 2018, now Pat. No. 10,806,452.

(60) Provisional application No. 62/549,679, filed on Aug. 24, 2017.

(51) Int. Cl.
*A61B 17/072* (2006.01)
*A61B 17/00* (2006.01)
*A61B 17/29* (2006.01)

(52) U.S. Cl.
CPC ...... *A61B 17/072* (2013.01); *A61B 17/07207* (2013.01); *A61B 2017/00473* (2013.01);
(Continued)

(58) Field of Classification Search
CPC ............ A61B 17/07207; A61B 17/072; A61B 17/068; A61B 2017/07228;
(Continued)

(56) References Cited

U.S. PATENT DOCUMENTS 3,079,606 A 3/1963 Bobrov et al.
3,490,675 A 1/1970 Green et al.
(Continued)

FOREIGN PATENT DOCUMENTS

JP 2013523212 A 6/2013
JP 2015535436 A 12/2015

OTHER PUBLICATIONS

Japanese Office Action dated Aug. 10, 2022, issued in corresponding JP Appln. No. 2018153108, 3 pages.

*Primary Examiner* — Andrew M Tecco
*Assistant Examiner* — Jacob A Smith

(57) ABSTRACT

A loading unit for use with a surgical instrument includes a body configured for coupling to a surgical instrument and defining a longitudinal axis and having proximal and distal ends, and an end effector coupled to the distal end of the body. The end effector includes a staple cartridge assembly having a staple cartridge and an anvil assembly having an anvil plate. A drive assembly is at least partially disposed within the body. The drive assembly includes an actuator member having a roller engageable with at least one of the staple cartridge assembly or the anvil assembly. The roller is configured to rotate upon longitudinal movement of the drive assembly to facilitate movement of the drive assembly and relative movement of the staple cartridge assembly and the anvil assembly between open and approximated conditions.

18 Claims, 10 Drawing Sheets

(52) U.S. Cl.
CPC ............ *A61B 2017/00477* (2013.01); *A61B 2017/07228* (2013.01); *A61B 2017/07257* (2013.01); *A61B 2017/07271* (2013.01); *A61B 2017/07285* (2013.01); *A61B 2017/2933* (2013.01)

(58) Field of Classification Search
CPC .......... A61B 2017/07271; A61B 2017/00473; A61B 2017/07257; A61B 2017/00477; A61B 2017/2933; A61B 2017/07285
USPC ........................................... 227/175.1–180.1
See application file for complete search history.

(56) References Cited

U.S. PATENT DOCUMENTS

| | | | |
|---|---|---|---|
| 5,954,259 A * | 9/1999 | Viola | A61B 17/07207 227/176.1 |
| 6,330,965 B1 * | 12/2001 | Milliman | A61B 17/07207 227/176.1 |
| 9,585,657 B2 | 3/2017 | Shelton, IV et al. | |
| 10,806,452 B2 | 10/2020 | Srinivas et al. | |
| 2004/0232201 A1 | 11/2004 | Wenchell et al. | |
| 2007/0163982 A1 * | 7/2007 | Lichinchi | B66C 19/02 212/175 |
| 2009/0182354 A1 * | 7/2009 | Blier | A61B 17/04 606/148 |
| 2009/0206124 A1 | 8/2009 | Hall et al. | |
| 2009/0206131 A1 | 8/2009 | Weisenburgh, II et al. | |
| 2013/0172929 A1 * | 7/2013 | Hess | A61B 17/07292 227/175.1 |
| 2014/0110456 A1 | 4/2014 | Taylor | |
| 2014/0224686 A1 | 8/2014 | Aronhalt et al. | |
| 2015/0122870 A1 * | 5/2015 | Zemlok | A61B 17/07207 227/176.1 |
| 2017/0086845 A1 | 3/2017 | Vendely | |

* cited by examiner

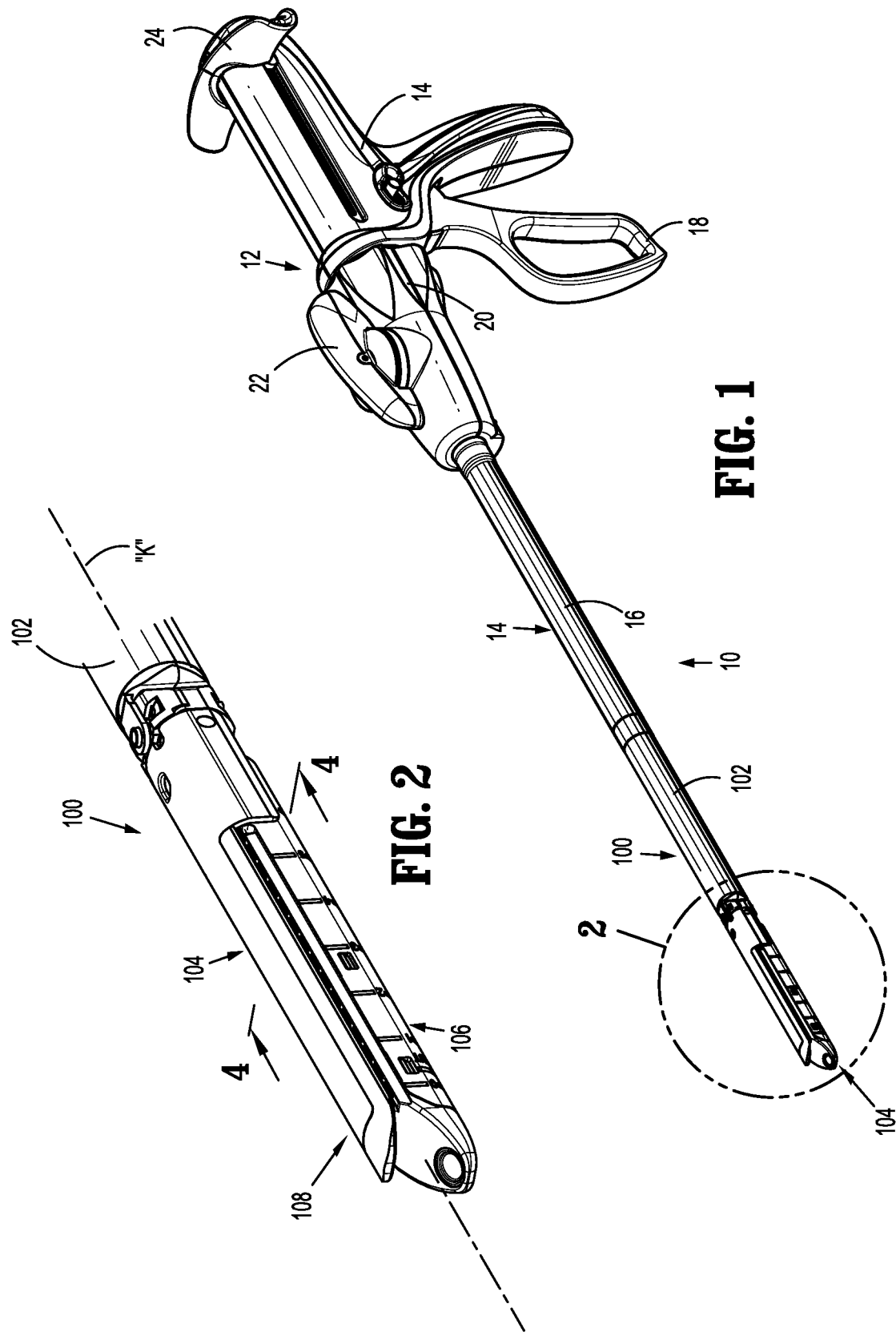

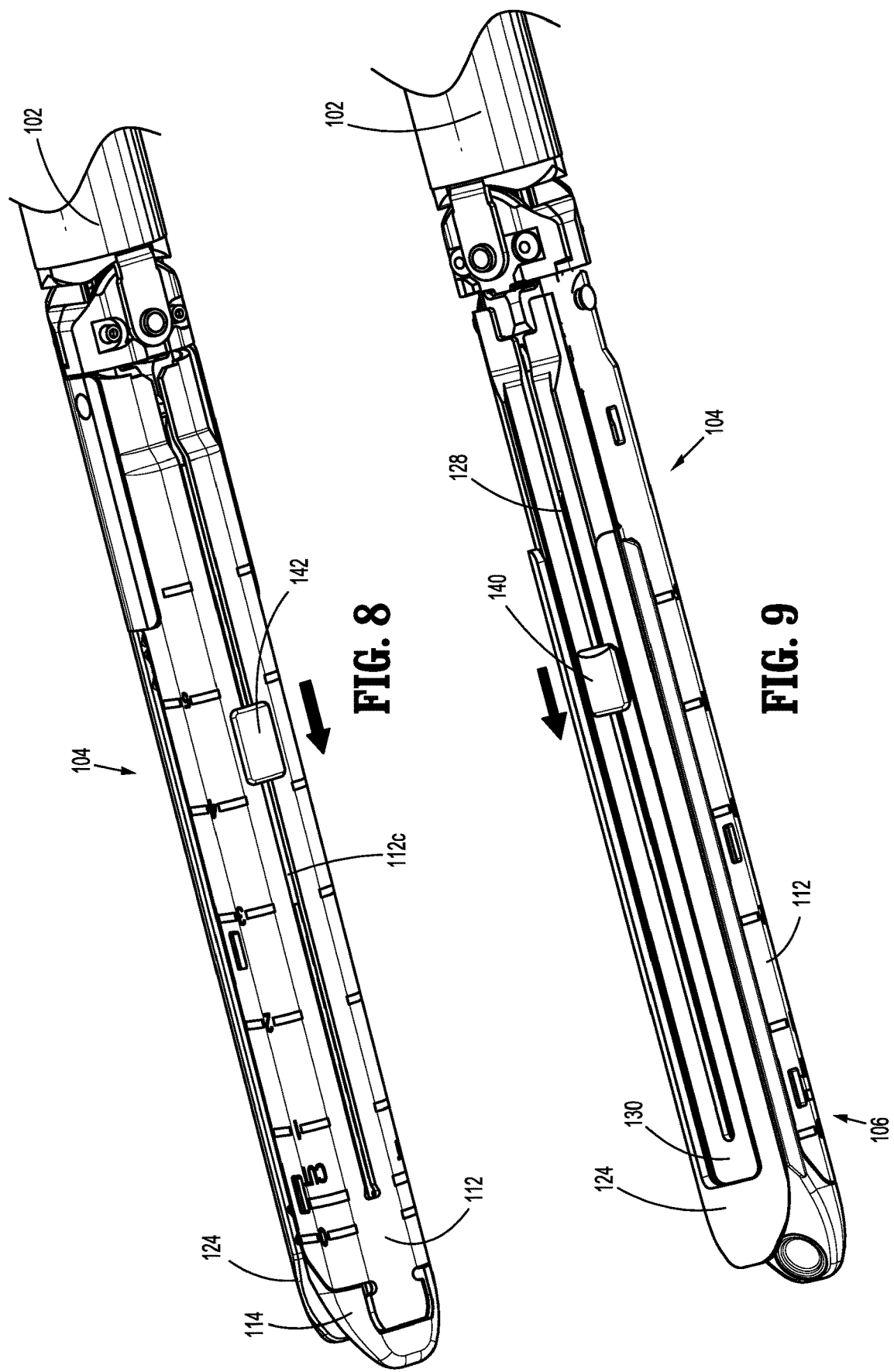

LOADING UNIT FOR A SURGICAL STAPLING INSTRUMENT

CROSS-REFERENCE TO RELATED APPLICATIONS

This application is a continuation of U.S. application Ser. No. 16/047,706 filed Jul. 27, 2018, now U.S. Pat. No. 10,806,452, which claims the benefit of and priority to U.S. Provisional Patent Application No. 62/549,679 filed Aug. 24, 2017. Each of these disclosures is incorporated by reference herein in its entirety.

BACKGROUND

1. Technical Field

The present disclosure relates to a surgical stapling instrument and, more particularly, relates to a disposable loading unit for use with a surgical stapling instrument and having a drive assembly with an actuator member which facilitates operation of the end effector associated with the loading unit.

2. Background of Related Art

Surgical stapling apparatuses for applying fasteners or staples to tissue are well known. These stapling apparatuses include single use devices which are preloaded with a supply of staples and are disposable after use. If the supply of staples is exhausted prior to completion of a surgical procedure, a new device may be required to complete the surgical procedure.

Certain stapling systems have replaceable components. These systems include a handle assembly and a replaceable loading unit. The loading unit may include a body and an end effector, and is attached to the handle assembly, and/or an adapter assembly associated with the handle assembly, prior to surgery. The end effector may include a staple cartridge which houses a plurality of staples and an anvil in opposition to the staple cartridge. A drive assembly is supported within the loading unit and is engageable with an associated drive mechanism of the handle assembly to both approximate the staple cartridge and the anvil, and to deploy the staples for deformation by the anvil. The staple cartridge may be removable and replaceable to fire more staples, or the replaceable loading unit can be replaced with a new, unfired loading unit having another set of staples. In other systems, only the staple cartridge can be removed and replaced, or the entire instrument is single use only.

Although these systems have provided significant clinical benefits, improvements are still possible. For example, it would be desirable to reduce the force(s) required to deploy the drive assembly of the loading unit to facilitate approximation of the staple cartridge and the anvil and/or facilitate delivery of the staples from the staple cartridge for formation against the anvil.

SUMMARY

Accordingly, the present disclosure is directed to a loading unit for use with a surgical instrument. The loading unit includes a body configured for coupling to a surgical instrument (e.g., a handle assembly), and defining a longitudinal axis and having proximal and distal ends, and an end effector coupled to the distal end of the body. The end effector includes a staple cartridge assembly having a staple cartridge with a plurality of staples and an anvil assembly having an anvil plate. A drive assembly is at least partially disposed within the body. The drive assembly includes an actuator member having a roller engageable with at least one of the staple cartridge assembly or the anvil assembly. The roller is configured to rotate upon longitudinal movement of the drive assembly to facilitate movement of the drive assembly and relative movement of the staple cartridge assembly and the anvil assembly between open and approximated conditions.

In embodiments, the actuator member defines at least one flange with the flange supporting the roller. In some embodiments, the actuator member includes a vertical connector and first and second flanges disposed on opposed sides of the vertical connector. In certain embodiments, each of the first and second flanges includes a roller whereby the roller of the first flange is configured for operative engagement with the anvil plate of the anvil assembly and the roller of the second flange is configured for operative engagement with the staple cartridge of the staple cartridge assembly. In embodiments, each of the first and second flanges includes a plurality of rollers. In some embodiments, each of the first and second flanges includes a roller mount secured thereto where each roller mount has openings for reception of respective rollers.

In certain embodiments, each of the first and second flanges includes a plurality of openings for reception of respective rollers. In embodiments, the openings of each of the first and second flanges are threaded, and each roller is coupled to a threaded member. The threaded member of each roller is threadably received within a respective threaded opening of each of the first and second flanges to mount the rollers to the first and second flanges.

In some embodiments, the actuator member includes a knife. In certain embodiments, the actuator member is engageable with a firing sled disposed within the staple cartridge of the staple cartridge assembly, whereby upon longitudinal movement of the drive assembly, the actuator member advances the firing sled to drive the staples from the staple cartridge for at least partial formation against the anvil plate of the anvil assembly.

The rollers incorporated within the actuator member of the loading unit rotate along respective surfaces of the staple cartridge assembly and the anvil assembly during longitudinal movement of the drive assembly thereby significantly reducing the forces required to advance the drive assembly and effect movement of the end effector between open and approximated conditions. These features advantageously improve performance of the surgical stapling instrument while enhancing usability for the clinician.

Other features of the present disclosure will be appreciated from the following description.

BRIEF DESCRIPTION OF THE DRAWINGS

Various aspects and features of the present loading units and surgical stapling instruments are described hereinbelow with reference to the drawings wherein like numerals designate identical or corresponding elements in each of the several views:

FIG. 1 is a perspective view of the surgical stapling instrument incorporating the loading unit of the present disclosure;

FIG. 2 is an enlarged perspective view of the end effector of the loading unit;

FIGS. 8 and 9 are first and second perspective views of the end effector of the loading unit illustrating longitudinal movement of the drive assembly and the actuator member relative to the end effector;

DETAILED DESCRIPTION

Figure 3:
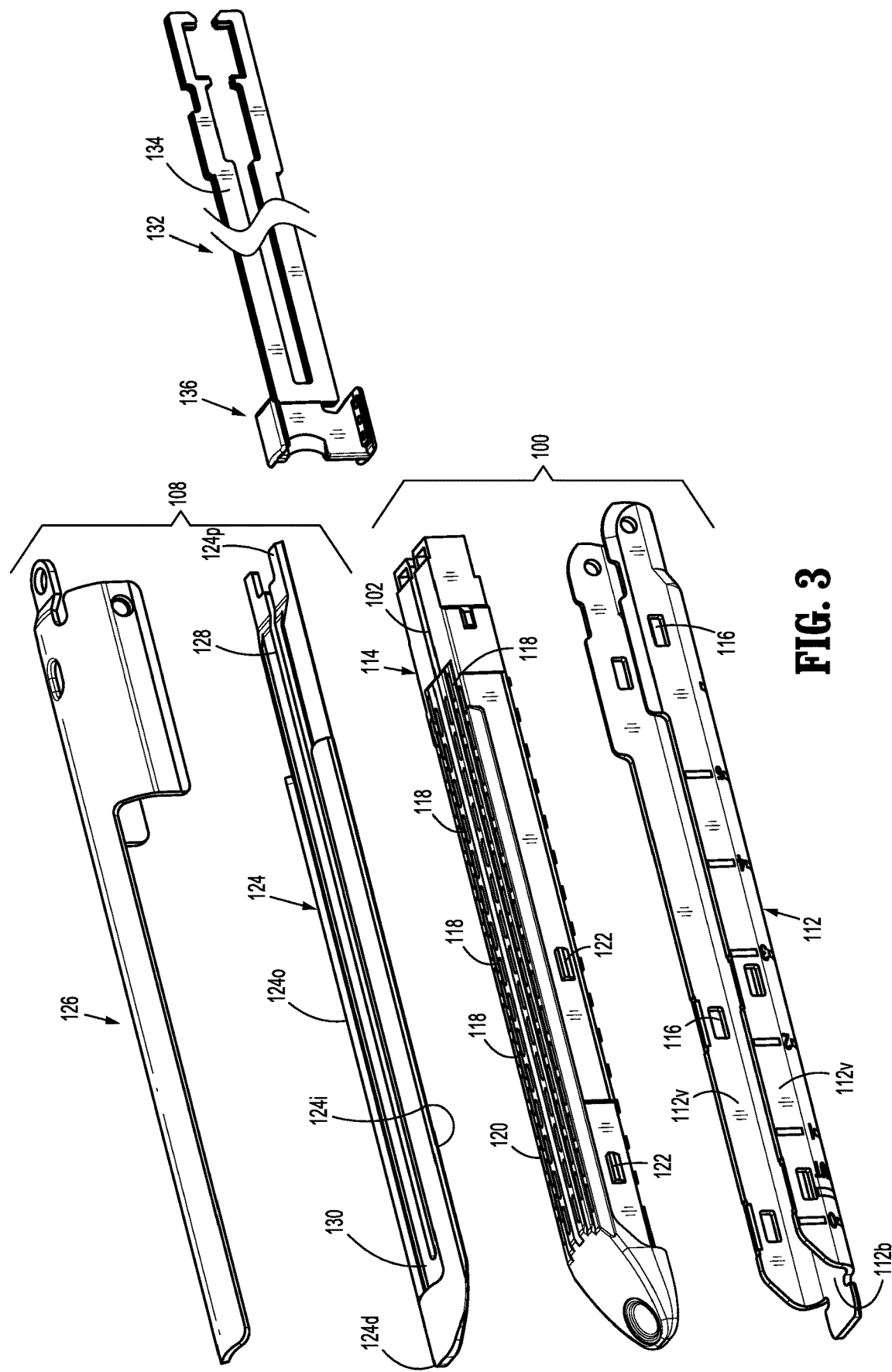
FIG. 3 is an exploded perspective view of the end effector illustrating the staple cartridge assembly, the anvil assembly and the drive assembly.

Embodiments of the presently disclosed loading unit for a surgical stapling instrument are described in detail with reference to the drawings, in which like reference numerals designate identical or corresponding elements in each of the several views. As used herein the term "distal" refers to that portion of the surgical stapling instrument, or component thereof, farther from the clinician, while the term "proximal" refers to that portion of the surgical stapling instrument, or component thereof, closer to the clinician.

Although the following discussion will focus on the surgical loading unit for use with a surgical stapling instrument, it is to be appreciated that the present disclosure encompasses both the loading unit and the surgical stapling instrument incorporating the loading unit.

In general, the present disclosure is directed to a loading unit which is connectable to a surgical handle assembly, e.g., a reusable handle assembly. The loading unit includes a staple cartridge assembly having a plurality staples and an anvil assembly in opposition to the staple cartridge assembly. The loading unit includes a drive assembly which is operatively couplable to the handle assembly. The drive assembly longitudinally advances upon actuation of the handle assembly to cause relative movement of the staple cartridge assembly and the anvil assembly to an approximated condition while also firing the staples from the staple cartridge assembly for formation against the anvil assembly. The drive assembly includes an actuator member having features, e.g., rollers, balls or ball bearings, which significantly reduce the driving force required to move the drive assembly thereby enhancing usability and comfort for the clinician.

Referring now to the drawings where like reference numerals indicate similar components throughout the several views, FIG. 1 illustrates a surgical stapling instrument 10 including the loading unit 100 of the present disclosure. The surgical stapling instrument 10 includes a handle assembly 12 having a handle frame 14 and an elongate member 16 extending from the handle frame 14. The handle assembly 12 may be any conventional handle incorporating one or more pushers, gears, linkages and/or drive components to control operation of the loading unit 100. In embodiments, the handle assembly 12 includes a movable trigger 18 mounted to the handle frame 14 for controlling operation of the loading unit 100 and a rotatable member 20 for rotating the elongate member 16 and the loading unit 100. The handle assembly 12 may further include an articulation lever 22 to articulate an end effector of the loading unit 100 and a retraction knob 24 to permit return of the trigger 18 and the associated drive components to their pre-fired condition subsequent to undergoing a firing stroke. The elongate member 16 includes mechanical components adapted to convert movement, e.g., rotation or linear movement, of the trigger 18 and the articulation lever 22 to control operation of the loading unit 100. Further details of a suitable handle assembly for use with the loading unit 100 may be ascertained by reference to commonly assigned U.S. Pat. No. 6,330,965 to Milliman and U.S. Pat. No. 8,968,276 to Zemlock et al., the entire contents of each disclosure being hereby incorporated by reference herein. In any of the embodiments disclosed herein, the loading unit can be configured for use with a robotic surgical system, or with a handle assembly having a motor.

Figure 4:
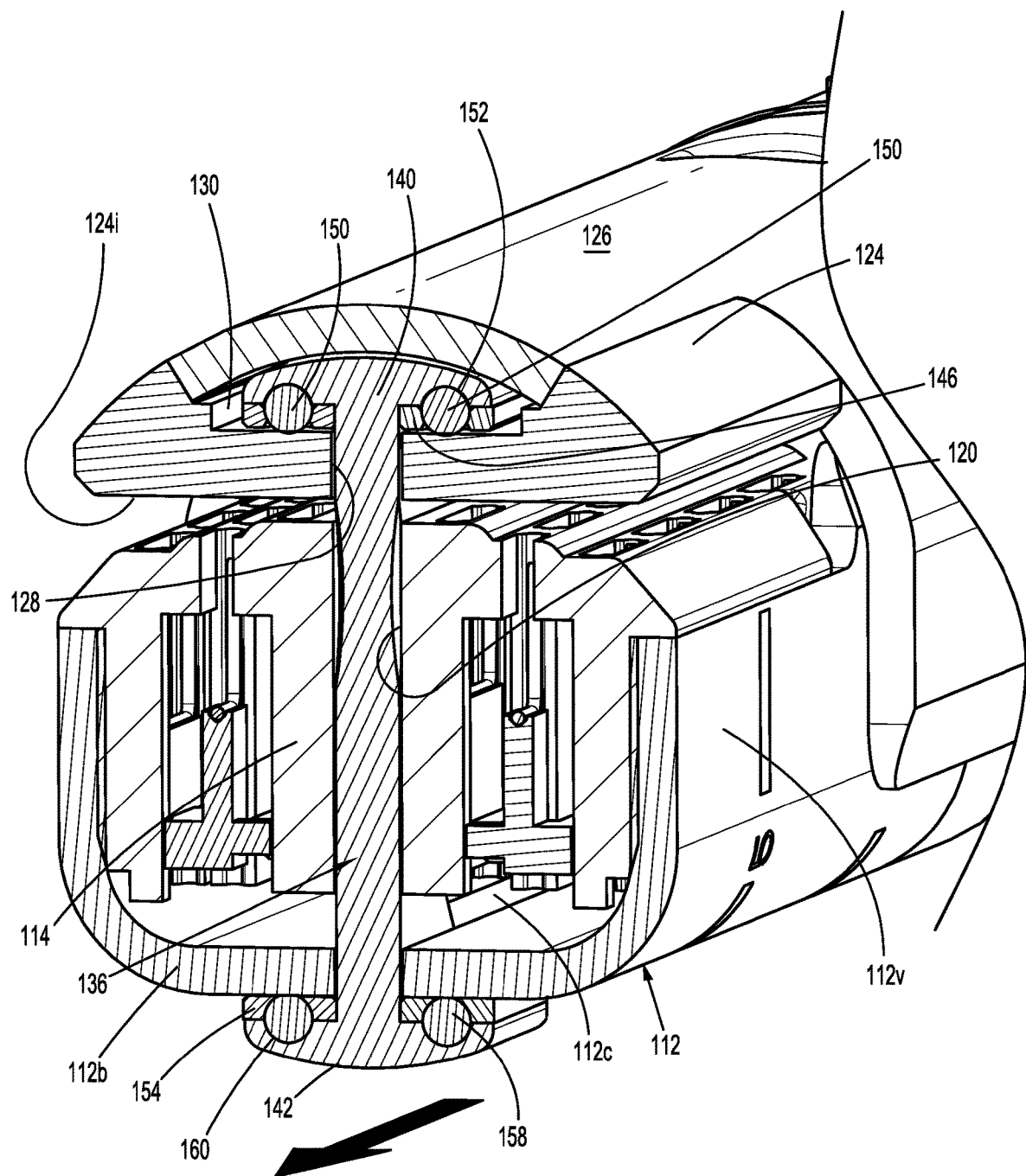
FIG. 4 is a cross-sectional view taken along the lines 4-4 of FIG. 2.

Referring now to FIGS. 2-4, in conjunction with FIG. 1, the loading unit 100 will be discussed. The loading unit 100 includes an elongate body 102 defining a longitudinal axis "k" (FIG. 2) and an end effector 104 coupled to the body 102. The body 102 is mounted to the elongate member 16 of the handle assembly 12. In embodiments, the body 102 is releasably mountable to the elongate member 16. The body 102 includes various pushers, links, gears etc. which couple with corresponding components within the elongate member 16 of the handle assembly 12 to control operation of the end effector 104.

The end effector 104 includes an elongate support channel 112 that receives a staple cartridge 114 and an anvil assembly 108. The support channel 112 is generally U-shaped in cross-section and consists of a bottom wall 112b and two vertical walls 112v depending from the bottom wall 112b. The bottom wall 112b further defines a central slot 112c (FIG. 4) extending along a major portion of the length of the support channel 112. The vertical walls 112v include various slots 116 which are spaced along the longitudinal axis "k". The staple cartridge 114 can be arranged with features that enable the staple cartridge 114 to be removed and replaced, or to be permanently affixed to the support channel 112.

The staple cartridge 114 includes at least one row, e.g., a plurality of rows, of staple receiving slots 118 for accommodating staples (not shown). In one embodiment, the staple cartridge 114 includes two sets of three rows of staple receiving slots 118 with the two sets being separated by a central slot 120 extending through the staple cartridge 114. The staple cartridge 114 also includes a plurality of tabs 122 which are received within the slots 116 of the support channel 112 to secure the staple cartridge 114 relative to the support channel 112.

The anvil assembly 108 includes an anvil plate 124 and an anvil cover 126 which is mounted over the anvil plate 124. The anvil plate 124 defines a central slot 128 extending along a majority of the longitudinal length of the anvil plate 124, e.g., from the proximal end 124p of the anvil plate 124 to a position adjacent the distal end 124d of the anvil plate 124. The central slot 128 of the anvil plate 124 is aligned with the central slot 120 of the staple cartridge 114. The inner anvil surface 124i of the anvil plate 124 is arranged in opposition to the staple cartridge 114 for crimping staples as they are driven from the staple receiving slots 118. The outer anvil surface 124o of the anvil plate 124 defines a recess 130 which extends along a major portion of each of the length and the width of the anvil plate 124. The anvil cover 126 is secured to the anvil plate 124 at the recess 130. Any methodologies for securing the anvil cover 126 to the anvil plate 124 are envisioned including adhesives, cements, fasteners, welding, etc.

The staple cartridge assembly 106 and the anvil assembly 108 are adapted for relative pivotal movement between an open condition and an approximated condition. In FIG. 2, the staple cartridge assembly 106 and the anvil assembly 108 are depicted in the approximated condition. In embodiments, the staple cartridge assembly 106 is pivotally mounted to the body 102 of the loading unit 100 and pivots relative to the body 102 to permit reception of tissue between the staple cartridge 114 and the anvil plate 124. In the alternative, the anvil assembly 108 may pivot relative to the body 102. Either or both the staple cartridge 114 and anvil assembly 108 may pivot, or move in some other fashion, to facilitate the receipt and clamping of tissue. The end effector 104 is also capable of pivoting laterally with respect to the elongate portion 14. Such movement is also referred to as "articulation".

Figure 5:
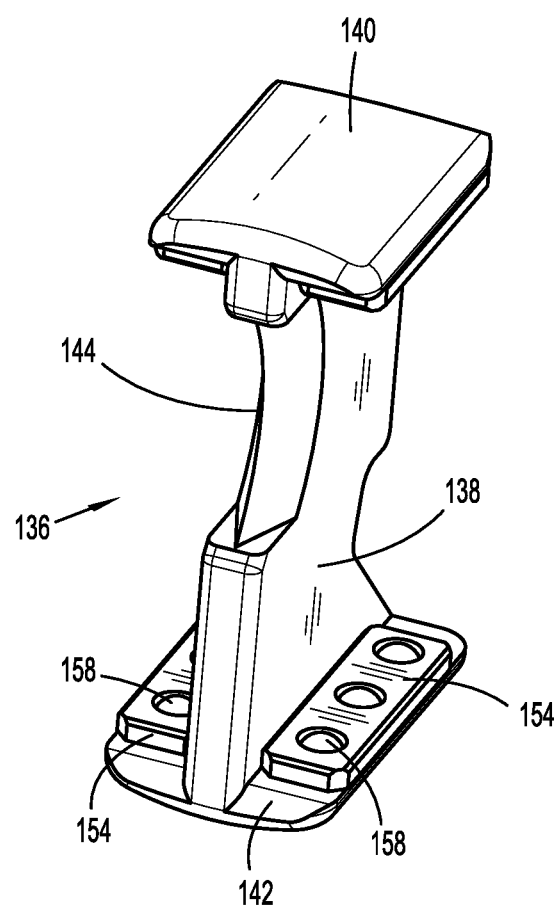
FIG. 5 is an enlarged perspective view of the actuator member of the drive assembly.

Referring now to FIGS. 3-5, the loading unit 100 further includes a drive assembly 132. The drive assembly 132 is operatively coupled to the handle assembly 12, and is at least partially disposed within the body 102 of the loading unit 100 when in an initial position of the drive assembly 132. Upon actuation of the trigger 18, the drive assembly 132 longitudinally moves through the end effector 104 to approximate the staple cartridge assembly 106 and the anvil assembly 108 and fire the staples. The drive assembly 132 includes a vertical central beam 134 extending along the length of the drive assembly 132 and an actuator member 136 mounted to, or integrally formed with, the central beam 134. The central beam 134 may be formed of more than one layer or component to enhance flexibility during articulation of the end effector 104.

Figure 7:
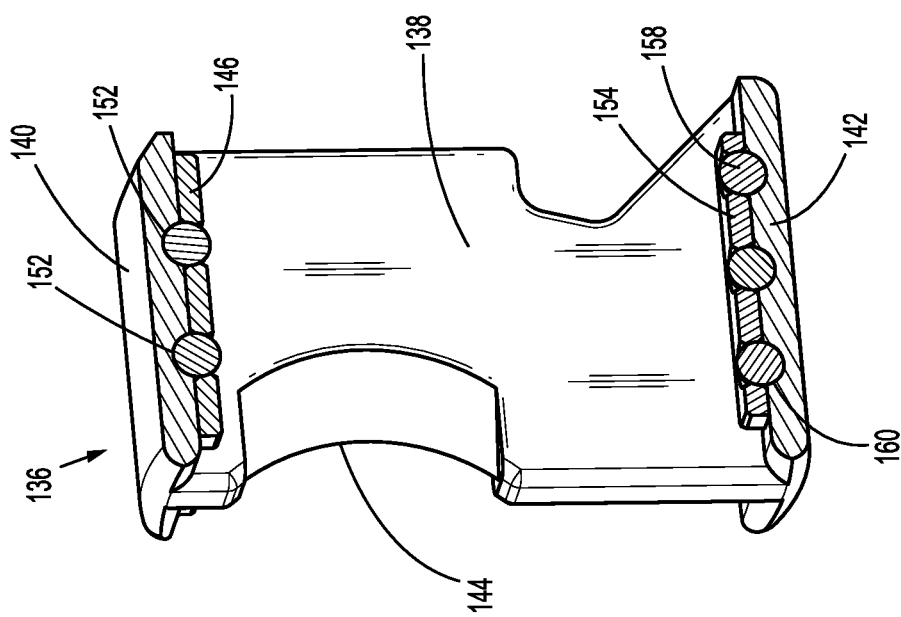
FIG. 7 is a perspective view and partial cross-section of the actuator member.
Figure 6:
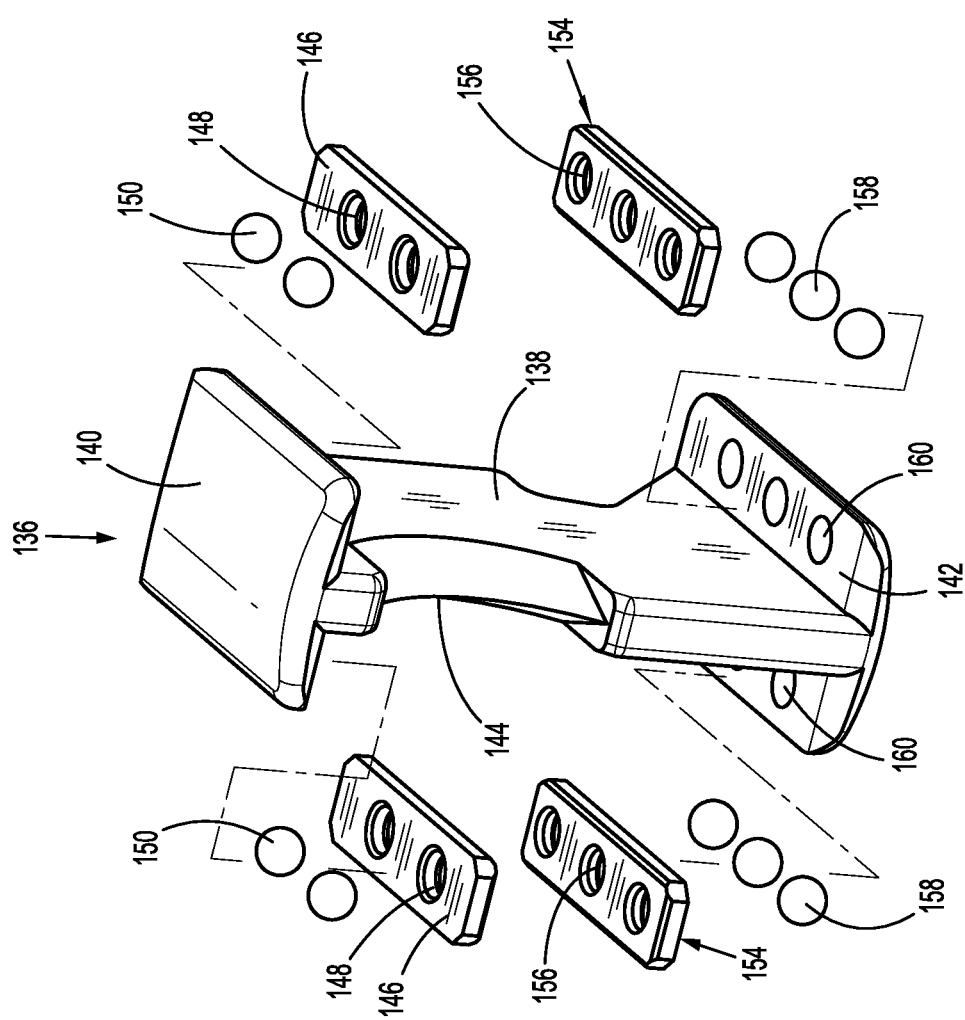
FIG. 6 is an exploded perspective view of the actuator member illustrating the roller mounts and the rollers.

Referring now to FIGS. 5-7, the actuator member 136 of the drive assembly 132 will be discussed. The actuator member 136 may be coupled to the central beam 134 by conventional methodologies such as welding, rivets or other connectors, etc., or may be monolithically formed with the central beam 134. The actuator member 136 includes a vertical connector 138 and first and second flanges 140, 142 coupled to the vertical connector 138 and arranged in diametrical opposed relation. The vertical connector 138 may include a knife 144 which is utilized to sever tissue during a firing stroke of the stapling instrument 10. The first flange 140 includes two roller mounts 146 with one roller mount 146 disposed on each side of the vertical connector 138. The roller mounts 146 may be secured to the first flange 140 through welding (e.g., laser welding) or by any methodologies. The roller mounts 146 each include openings 148 therethrough and a roller 150, mounted within each opening 148. The rollers 150 can be shaped as a ball or cylinder and are mounted to allow their rotation. The rollers 150 may be fabricated from a hard material such as stainless steel or a rigid polymer. The first flange 140 further includes arcuate (e.g., at least partially circular) recesses 152 within its inner surface, which are in registration with the openings 148 of the roller mounts 146. The rollers 150 rotate within the openings 148 of the roller mounts 146 and the arcuate recesses 152 of the first flange 140 during traversing movement of the drive assembly 132 and the actuator member 136. In the illustrated embodiment, the first flange 140 includes roller mounts 146 having two openings 148 and two rollers 150. Fewer or more rollers can be used.

The arcuate recesses 152 can be omitted, and the surfaces of the flange 140 and roller or rollers 150 can be shaped to reduce friction. The materials on the flange 140, roller 150, and/or roller mount 146 can be selected to reduce friction or other friction-reducing techniques can be used, such as polishing or polymeric coatings.

The second flange 142 includes two roller mounts 154 having three openings 156 and associated rollers 158 at least partially positioned therein. The second flange 142 also includes arcuate recesses 160 within its internal surface for at least partial reception of the rollers 158. The rollers 158 function in a similar manner by rotating within the openings 156 of the roller mounts 154 and the arcuate recesses 160 of the internal surface of the second flange 142 during traversing movement of the drive assembly 132 and the actuator member 136.

As best depicted in FIG. 4, the rollers 150 of the roller mounts 146 of the first flange 140 contact the surface defining the recess 130 of the anvil plate 124. The rollers 158 of the roller mounts 154 of the second flange 142 contact the outer surface of the support channel 112 of the staple cartridge assembly 106. In addition, the vertical connector 138 of the actuator member 136 extends through the respective central slots 120, 128 of the staple cartridge 114 and the anvil plate 124, and through the central slot 112c of the support channel 112. The first flange 140 of the actuator member 136 is disposed within the recess 130 of the anvil plate 124 and the second flange 142 is external of the support channel 112 of the staple cartridge assembly 106.

FIGS. 8-9 illustrate the actuator member 136 moving in a longitudinal direction in response to movement of the drive assembly 132 through actuation of the trigger 18. In FIG. 9, the anvil cover 126 is removed for illustrative purposes. The vertical connector 138 of the actuator member 136 traverses the central slots 120, 128 in the staple cartridge 114 and the anvil plate 124 and the central channel 112c of the support channel 112 while the first and second flanges 140, 142 contact and slide along the respective outer surface defining the recess 130 of the anvil plate 124 of the anvil assembly 108 and the support channel 112 of the staple cartridge assembly 106 during movement of the drive assembly 132 and the actuator member 136 from the initial position toward an actuated position. During this movement, the rollers 150, 158 of the roller mounts 146, 154 of each of the first and second flanges 140, 142 rotate or roll along the respective surfaces thereby facilitating traversal of the actuator member 136 and the drive assembly 132 relative to the end effector 104.

Figure 10:
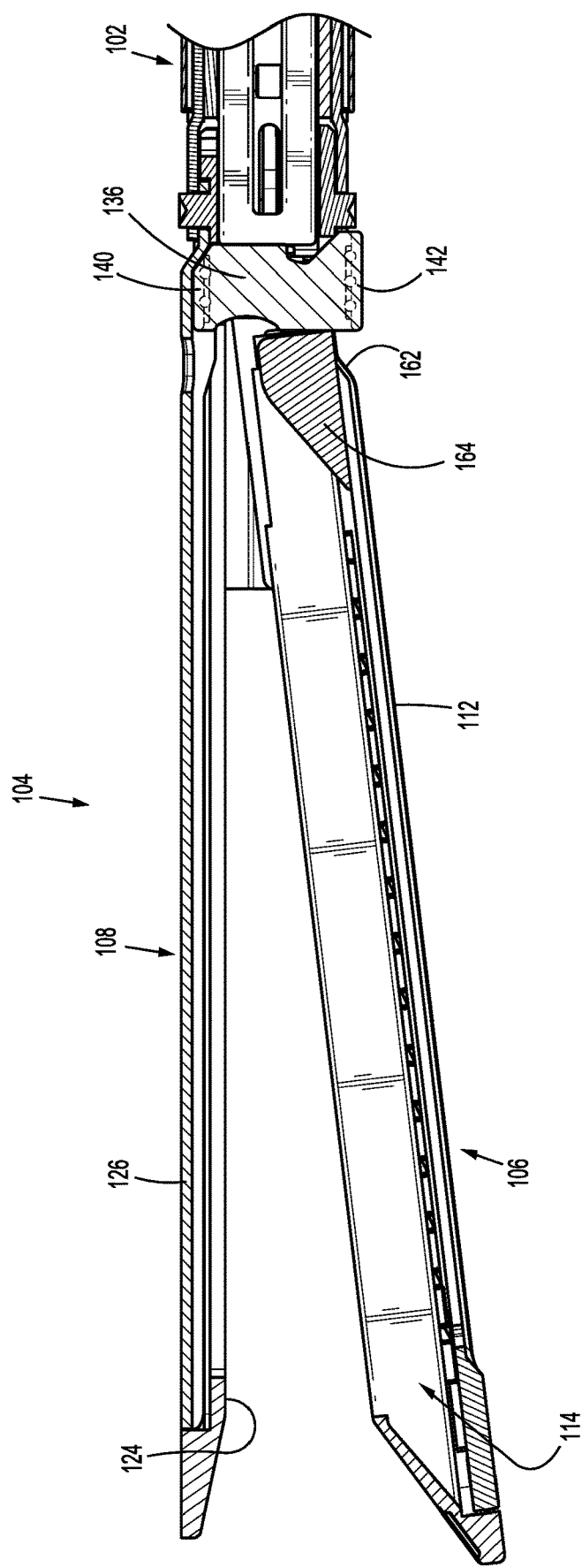
FIG. 10 is a side cross-sectional view illustrating the staple assembly and the anvil assembly of the end effector in an open condition and the drive assembly and the actuator member in an initial position.
Figure 11:
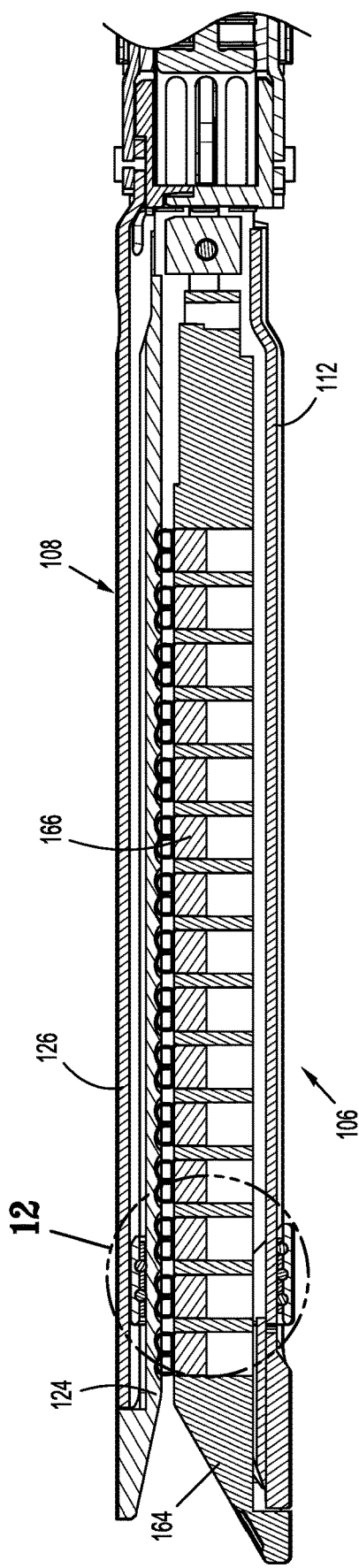
FIG. 11 is a side cross-sectional view illustrating the drive assembly and the actuator member in an actuated position with the staple assembly and the anvil assembly in an approximated condition.
Figure 12:
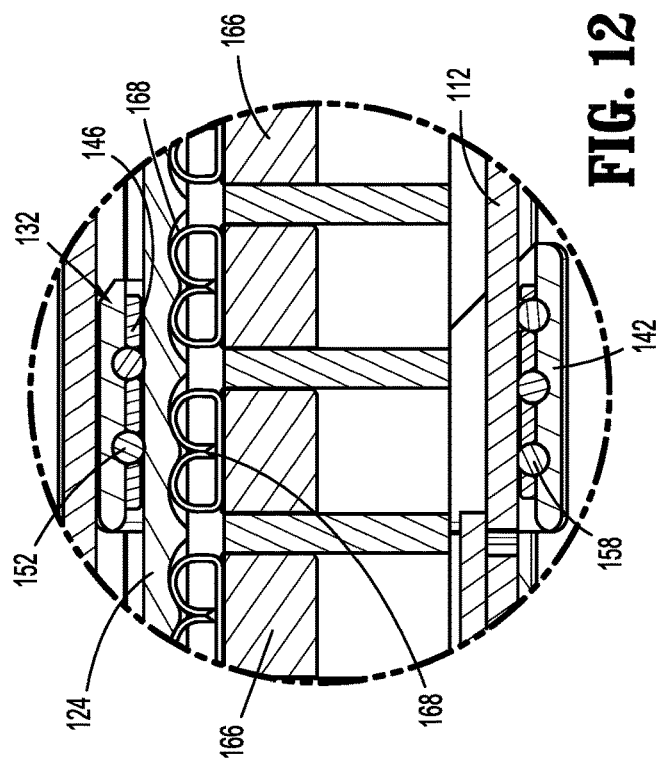
FIG. 12 is an enlarged view of the area of detail depicted in FIG. 11 illustrating the staple pushers driving the staples against the anvil plate upon movement of the drive assembly and the actuator member to the actuated position.

The use of the loading unit 100 in stapling tissue will now be discussed. Tissue to be treated, e.g., in conjunction with a laparoscopic surgical procedure, is identified. The end effector 104 in the open condition of FIG. 10 is manipulated to position the tissue between the staple cartridge 114 and the anvil plate 124. The trigger 18 is actuated causing the drive assembly 132 and the actuator member 136 to advance in a longitudinal direction. During initial advancing movement, the second flange 142 contacts a cam surface 162 (FIG. 10) of the staple cartridge 114 to move the staple cartridge assembly 106 to the approximated condition. In addition, the actuator member 136 engages a firing sled 164 disposed within the staple cartridge 114 to advance the firing sled 164. Continued advancing movement of the actuator member 136 and the drive assembly 132 locks the end effector 104 in the approximated condition as depicted in FIG. 11. In addition, the firing sled 164 continues its advancing movement, and engages the staple pushers 166 within the staple receiving slots 118 of the staple cartridge 114 to fire the staples 168 through the tissue for formation against the anvil plate 124 (FIG. 12). During the traversing movement of the drive assembly 132, the actuator member 136 slides relative to the staple cartridge 114 and the anvil plate 124 with relative ease as facilitated by spinning of the rollers 150, 158, thereby reducing the forces required to approximate the staple cartridge assembly 106 relative to the anvil assembly 108 and to drive the firing sled 164 to fire the staples 168.

Figure 13:
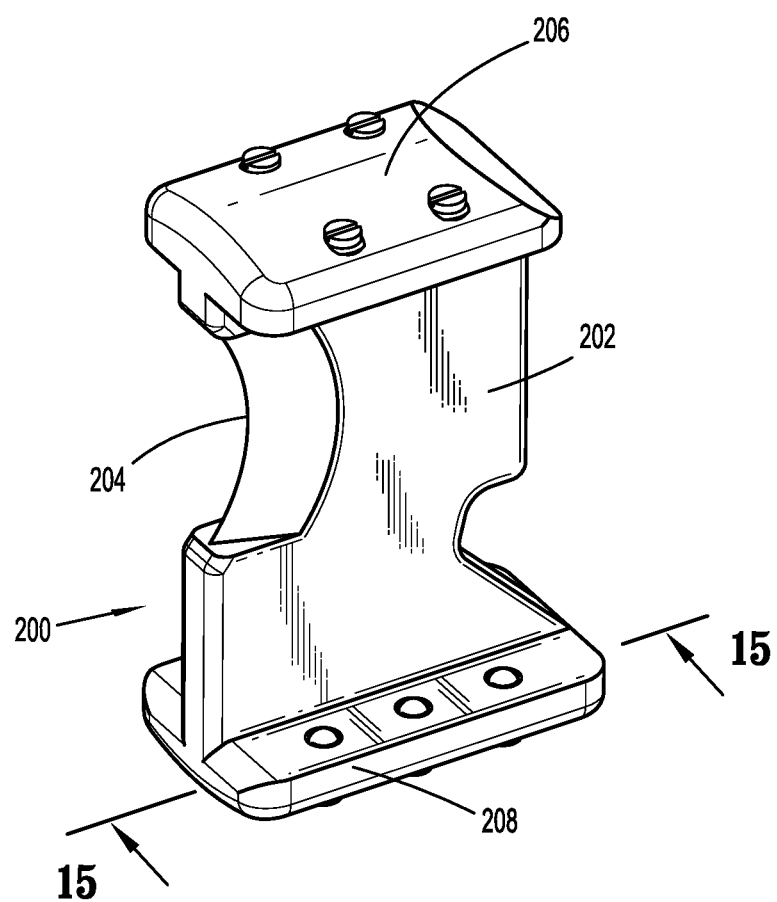
FIG. 13 is a perspective view of one embodiment of the actuator member of the drive assembly.
Figure 15:
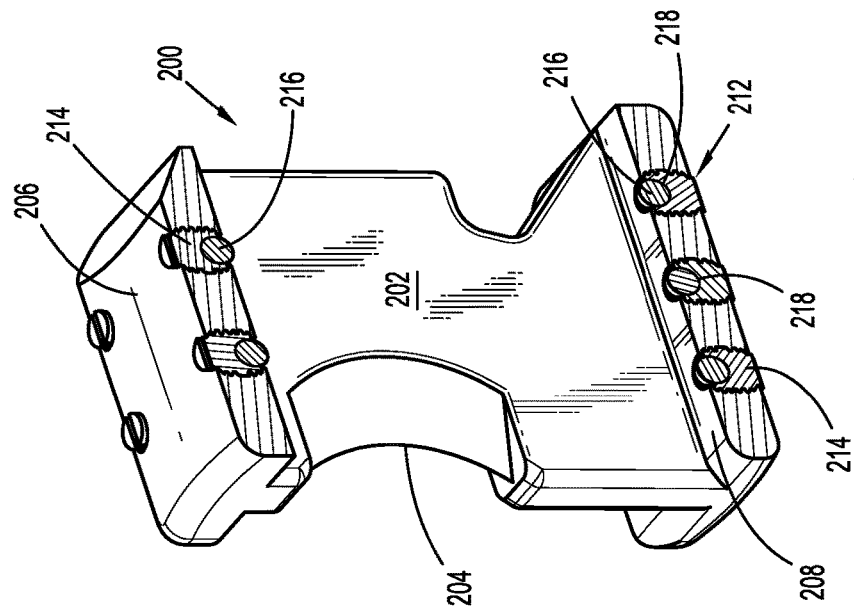
FIG. 15 is a perspective view in cross-section of the actuator member of FIG. 13.
Figure 14:
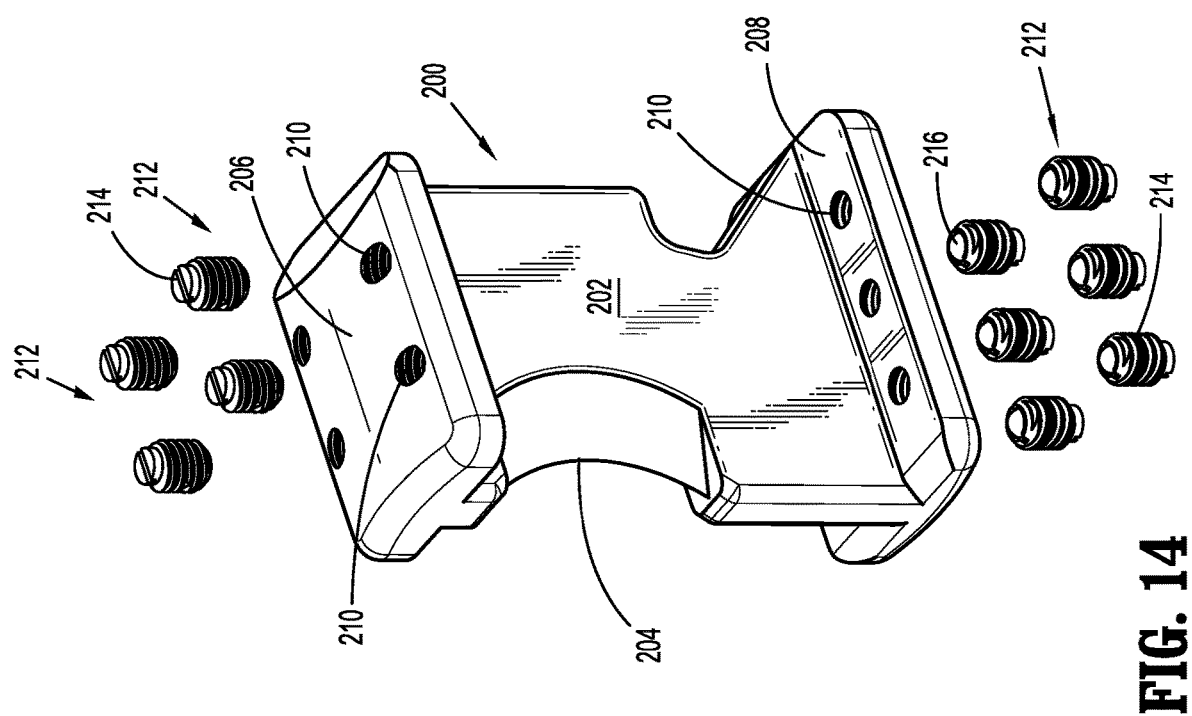
FIG. 14 is an exploded perspective view of the actuator member of FIG. 13.

FIGS. 13-15 illustrate another embodiment of the actuator member of the drive assembly, which can be incorporated within the loading unit 100 of the present disclosure. The actuator member 200 includes a vertical connector 202 having a knife 204 and first and second flanges 206, 208 disposed on opposed ends of the connector 202. The first and second flanges 206, 208 each includes a plurality of threaded openings 210. The actuator member 200 further includes threaded roller assemblies 212. Each threaded roller assembly 212 includes a threaded member 214 and a roller 216, which is supported by the threaded member 214. The threaded members 214 are configured to be threaded and secured within the threaded openings 210. In embodiments, the rollers 216 are each received within a recess 218 of the threaded member 214 and are capable of rotation within the recesses 218. In other embodiments, the rollers 216 are fixed within the recesses 218 of the threaded members 214. The first flange 206 includes two sets of two threaded roller assemblies 212 and associated threaded openings 210 and the second flange 208 includes two sets of three threaded roller assemblies 212 with associated threaded openings 210. The two sets of each of the first and second flanges 206, 208 are disposed on opposed sides of the vertical connector 202. The actuator member 200 is secured to the drive assembly 132 and operates in a similar manner to the actuator member 136 described in connection with FIGS. 1-12. In the embodiment where the rollers 216 are fixed within the threaded members 214, the rollers 216 will provide a relatively small contact surface with the staple cartridge 114 and/or the anvil plate 124 thereby minimizing friction and reducing the force required to approximate the staple cartridge assembly 106 relative to the anvil assembly 108 and to fire the staples.

The various embodiments disclosed herein may also be configured to work with robotic surgical systems and what is commonly referred to as "Telesurgery." Such systems employ various robotic elements to assist the surgeon and permit remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions. One suitable surgical robotic system is disclosed in commonly assigned U.S. Patent Publication No. 2015/0297199 to Nicholas et al., the entire contents of which are hereby incorporated by reference herein.

From the foregoing and with reference to the various figure drawings, those skilled in the art will appreciate that certain modifications can also be made to the present loading units and surgical stapling instruments without departing from the scope of the present disclosure. For example, the drive assembly described above includes a longitudinally movable beam, but in other embodiments, the drive assembly could include a rotatable drive shaft. While several embodiments of the loading units and surgical stapling instruments disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. No representation is made that the drawings are exactly to scale.

What is claimed is:
1. A surgical instrument, comprising:
a body having proximal and distal portions;
an end effector coupled to the distal portion of the body, the end effector including:
a cartridge assembly including a staple cartridge having a plurality of staples; and an anvil assembly including an anvil plate, the anvil assembly pivotably coupled to the cartridge assembly such that the end effector is movable between open and approximated conditions; and a drive assembly movable in relation to the end effector between retracted and advanced positions, the drive assembly including an actuator member having a first flange engaged with the anvil assembly, a second flange engaged with the cartridge assembly, and a vertical connector connecting the first flange to the second flange, the first flange supporting at least three first rollers on each side of the vertical connector and the second flange supporting at least three second rollers on each side of the vertical connector, the at least three first rollers engaging the anvil assembly and the at least three second rollers engaging the cartridge assembly, the at least three first and second rollers being rotatable in response to movement of the drive assembly between the retracted and advanced positions.

2. The surgical instrument of claim 1, wherein each of the first and second flanges includes a roller mount positioned on each side of the vertical connector, each of the roller mounts defining openings, each of the openings receiving one of the first or second rollers.

3. The surgical instrument of claim 2, wherein the openings of each of the roller mounts are threaded, and wherein each of the at least three first and second rollers is retained within one of the openings by a threaded member.

4. The surgical instrument of claim 3, wherein each of the at least three first and second rollers is coupled to a respective one of the threaded members.

5. The surgical instrument of claim 2, wherein each of the roller mounts is secured to one of the first or second flanges by welding.

6. The surgical instrument of claim 5, wherein each of the at least three first and second rollers includes a ball that is rotatably positioned within one of the openings.

7. The surgical instrument of claim 1, wherein the actuator member includes a knife that is supported on the vertical connector.

8. The surgical instrument of claim 1, wherein the cartridge assembly includes a firing sled, the actuator member engageable with the firing sled when the drive assembly moves from its retracted position towards its advanced position to advance the firing sled within the cartridge assembly from a retracted position towards an advanced position to drive the staples from the staple cartridge.

9. The surgical instrument of claim 1, wherein each of the first and second flanges defines arcuate recesses, and each of the at least three first and second rollers is received within one of the arcuate recesses.

10. The surgical instrument of claim 1, further including a handle assembly, the proximal portion of the body coupled to the handle assembly.

11. A surgical instrument, comprising:
a body having proximal and distal portions;
an end effector coupled to the distal portion of the body, the end effector including:
a cartridge assembly including a staple cartridge having a plurality of staples; and
an anvil assembly including an anvil plate, the anvil assembly pivotably coupled to the cartridge assembly such that the end effector is movable between open and approximated conditions; and
a drive assembly movable in relation to the end effector between retracted and advanced positions, the drive assembly including an actuator member having a first flange engaged with the anvil assembly, a second flange engaged with the cartridge assembly, and a vertical connector connecting the first flange to the second flange, the first flange supporting first rollers on each side of the vertical connector and the second flange supporting second rollers on each side of the vertical connector, the first rollers engaging the anvil assembly and the second rollers engaging the cartridge assembly, the first and second rollers being rotatable in response to movement of the drive assembly between the retracted and advanced positions, wherein each of the first and second rollers is in the form of a ball.

12. An end effector comprising:
a cartridge assembly including a staple cartridge having a plurality of staples;
an anvil assembly including an anvil plate, the anvil assembly pivotably coupled to the cartridge assembly such that the end effector is movable between open and approximated conditions; and
a drive assembly movable in relation to the cartridge and anvil assemblies between retracted and advanced positions, the drive assembly including an actuator member having a first flange engaged with the anvil assembly, a second flange engaged with the cartridge assembly, and a vertical connector connecting the first flange to the second flange, at least one of the first or second flanges supporting at least three rollers on each side of the vertical connector, the at least three rollers engaging one of the cartridge and anvil assemblies and being rotatable in response to movement of the drive assembly between its retracted and advanced positions.

13. The end effector of claim 12, wherein the at least one of the first or second flanges includes a roller mount positioned on each side of the vertical connector, each of the roller mounts defining openings, each of the openings receiving one of the at least three rollers.

14. The end effector of claim 13, wherein the openings of each of the roller mounts are threaded and each of the at least three rollers is retained within one of the openings by a threaded member.

15. The end effector of claim 12, wherein the actuator member includes a knife that is supported on the vertical connector.

16. The end effector of claim 12, wherein the cartridge assembly includes a firing sled, the actuator member engageable with the firing sled when the drive assembly moves from its retracted position towards its advanced position to advance the firing sled within the cartridge assembly from a retracted position towards an advanced position to drive the staples from the staple cartridge.

17. The end effector of claim 12, wherein each of the at least three rollers is in the form of a ball.

18. The end effector of claim 12, wherein the at least one of the first or second flanges defines arcuate recesses, and each of the at least three rollers is received within one of the arcuate recesses.

* * * * *